United States Patent
Stüwe et al.

(10) Patent No.: US 6,175,049 B1
(45) Date of Patent: Jan. 16, 2001

(54) PROCESS FOR THE PRODUCTION OF 1, 2-BUTADIENE

(75) Inventors: Arnd Stüwe, Leverkusen; Jürgen Linnemann, Neuss; Jens Herwig, Köln; Christian Gabel, Dormagen; Bernd Hohmann, Dormagen; Joachim Grub, Dormagen, all of (DE)

(73) Assignee: EC Erdolchemie GmbH (DE)

( * ) Notice: Under 35 U.S.C. 154(b), the term of this patent shall be extended for 0 days.

(21) Appl. No.: 09/375,896

(22) Filed: Aug. 17, 1999

(30) Foreign Application Priority Data

Aug. 27, 1998 (DE) ................................. 198 38 932

(51) Int. Cl.$^7$ ....................................... C07C 7/04
(52) U.S. Cl. ................. 585/810; 203/9; 208/347
(58) Field of Search ...................... 585/810, 601; 203/9; 208/347, 48 AA

(56) References Cited

U.S. PATENT DOCUMENTS 3,859,377 * 1/1975 Gross et al. ..................... 260/681.5

FOREIGN PATENT DOCUMENTS

| 2 331 547 | 1/1974 | (DE) . |
| 246 009 | 5/1987 | (DE) . |
| 1 384 852 | 2/1975 | (GB) . |

OTHER PUBLICATIONS

Derwent English Abstract for DE 2331547 (Jan. 17, 1974).
Derwent English Abstract for DD 246009 (May 27, 1987).

* cited by examiner

*Primary Examiner*—Bekir L. Yildirim
(74) *Attorney, Agent, or Firm*—Connolly Bove Lodge & Hutz LLP

(57) ABSTRACT

The production of 1,2-butadiene in purities of at least 85% becomes possible by means of a process in which a polymerization-inhibitor-containing $C_4$ hydrocarbon fraction is subjected to at least one fractional distillation.

20 Claims, No Drawings

PROCESS FOR THE PRODUCTION OF 1, 2-BUTADIENE

BACKGROUND OF THE INVENTION

1. Field of the Invention

The present invention relates to a process for the production of 1,2-butadiene from a polymerization-inhibitor-containing $C_4$ hydrocarbon fraction by fractional distillation.

2. Description of the Prior Art

It is not possible to isolate 1,3-butadiene from a mixture of $C_4$ hydrocarbons by simple distillation, since all components boil in a very narrow temperature range and, furthermore, some form azeotropic mixtures. For this reason, 1,3-butadiene is currently produced on an industrial scale by the extractive distillation principle. In this process, a solvent is fed in an extraction column to a gaseous $C_4$ hydrocarbon mixture from naphtha or middle distillate pyrolysis. This solvent primarily dissolves 1,3-butadiene, which is selectively extracted as a result. The 1,3-butadiene-containing solvent thus remains in the bottom of the column, while the residual $C_4$ fraction distils off overhead. As solvent, use is made, for example, of sulfolane, N-methylpyrrolidone (NMP), dimethylformamide, acetonitrile or dimethylacetamide. To avoid the unwanted thermal polymerization of 1,3-butadiene in the course of the extractive distillation, polymerization inhibitors are added both to the feed fraction of the extractive distillation and to the bottom product of solvent and 1,3-butadiene. These polymerization inhibitors are, for example, 4-tert-butylcatechol (TBC). In the course of the subsequent separation operations for purifying the 1,3-butadiene, distillation residues of $C_4$ and $C_5$ hydrocarbons which comprise these polymerization inhibitors, sometimes in considerable amounts, therefore arise. It is generally customary to destroy distillation residues or bottom products of this type from the purification of 1,3-butadiene. This is generally performed by combustion via a flare or by other thermal utilization. In this procedure, valuable hydrocarbons which are suitable for material utilization are lost.

DD 246 009 discloses a process for working up such distillation residues which arise in the extractive distillation of $C_4$ hydrocarbon fractions for the production of 1,3-butadiene and comprise dissolved polymerization inhibitors. In this process, the inhibitor/$C_4$ hydrocarbon mixture is firstly introduced into a preferably aromatics-containing hydrocarbon mixture whose initial boiling point is 50–200K higher than the boiling point of the $C_4$ hydrocarbon fraction and is then thermally treated. In this case the temperature is set so that the $C_4$ hydrocarbon fraction evaporates and can thus be completely removed. In the bottom of the column accordingly remains a mixture of the higher-boiling, preferably aromatic hydrocarbons, in particular $C_8$- and $C_9$ aromatics, the high boilers, the contaminants and the polymerization inhibitor. This process thus makes it possible to separate off the $C_4$ hydrocarbon fraction as such from the contaminants and high boilers and also, in particular, from the inhibitor. The total $C_4$ hydrocarbon fraction is passed to material or caloric utilization; further fractionation into the various components is not described.

However, it is desirable to produce the individual compounds from $C_4$ hydrocarbon fractions of this type. Especially the $C_4$ component 1,2-butadiene is increasingly gaining importance and is used as polymerization regulator in the preparation of synthetic rubber from 1,3-butadiene. 1,2-butadiene is also a synthesis building block of interest for the production of perfumes. Thus, the reaction of 1,2-butadiene with acetaldehyde gives cis-3-hexenol, i.e. leaf alcohol.

The object of the present invention was thus to provide a process which enables the production of pure 1,2-butadiene in a simple manner from $C_4$ hydrocarbon fractions.

SUMMARY OF THE INVENTION

This object is achieved by a process for the production of 1,2-butadiene in which a polymerization-inhibitor-containing $C_4$ hydrocarbon fraction is subjected to at least one fractional distillation.

DESCRIPTION OF THE PREFERRED EMBODIMENT

It is surprising that the separation and production of pure 1,2-butadiene from $C_4$ hydrocarbon mixtures succeeds without prior separation of the polymerization inhibitor and without other additives of other higher-boiling hydrocarbon fractions. Owing to the considerable content of inhibitor in the starting mixture to be distilled 3 and the further concentration of this inhibitor in the course of the fractional distillation it was to be expected that the inhibitor would increasingly crystallize out, since the solubility of inhibitors in hydrocarbon mixtures is only very low. In isopentane, the polymerization inhibitor TBC dissolves only to 0.5%, for example, at 20° C. Such a crystallization out of the inhibitor should lead to a coating of the distillation column which would be accompanied by column blockages and thus impairment of the separation efficiency. However, unexpectedly, none of these phenomena occur in the process according to the invention.

The feed stream for the process according to the invention is customarily obtained by taking off the polymerization-inhibitor-containing $C_4$ hydrocarbon fraction from the bottom of a distillation column or at a suitable plate in the stripping section of a distillation column which is producing 1,3-butadiene at the top as pure product.

This polymerization-inhibitor-containing $C_4$ hydrocarbon fraction has a boiling range from −15° C. to +45° C. In addition to low-boiling $C_4$ components, such as butanes, 1,3-butadiene, butenes and $C_4$ acetylenes, it also contains the wanted material of value 1,2-butadiene. As high-boiling compounds, $C_5$ hydrocarbons, such as 3-methyl-1-butene and isopentane are found in the $C_4$ hydrocarbon fraction. In addition, in the $C_4$ hydrocarbon mixture, polymerization inhibitors such as the abovementioned TBC are always present. Depending on the distillation technique used to purify the 1,3-butadiene, the concentrations of the individual components in the $C_4$ hydrocarbon mixture fluctuate within a broad range. Usually, 0–5% by weight of saturated $C_4$ hydrocarbons, 5–30% by weight of butenes, 10–55% by weight of 1,3-butadiene, 0.1–2% by weight of $C_4$ acetylenes, 20–65% by weight of 1,2-butadiene, 5–20% by weight of $C_5$ hydrocarbons and 0.2–2% by weight of polymerization inhibitor are present in the polymerization-inhibitor-containing $C_4$ hydrocarbon mixture. A content of low-boilers or high-boilers deviating from this does not interfere in the process according to the invention, but may require adaptations of the distillation conditions (temperature, reflux ratio) and the distillation equipment (column diameter, number of theoretical plates). Preferably, in the process according to the invention, use is made of $C_4$ hydrocarbon mixtures in which 0–1% by weight of saturated $C_4$ hydrocarbons, 10–20% by weight of butenes, 20–55% by weight of 1,3-butadiene, 0.1–1% by weight of $C_4$ acetylenes, 30–65% by weight of 1,2-butadiene, 5–10% by weight of $C_5$ hydrocarbons and 0.2–1% by weight of polymerization inhibitor are present.

According to an embodiment of the process according to the invention, a procedure is carried out such that a) in a first fractional distillation of the polymerization-inhibitor-containing $C_4$ hydrocarbon fraction, the low-boiling $C_4$ hydrocarbons are taken off as first overhead product and a fraction which comprises 1,2-butadiene, the $C_5$ hydrocarbons and the polymerization inhibitor is taken off as first bottom product and b) the first bottom product is fed to a second fractional distillation and there the 1,2-butadiene is produced as second overhead product and the $C_5$ hydrocarbons and the polymerization inhibitor are produced as second bottom product. In this embodiment, the first overhead product comprises the low-boiling $C_4$ hydrocarbons such as 1,3-butadiene and the butenes. The first bottom product, which comprises the wanted 1,2-butadiene, the $C_5$ hydrocarbons and the polymerization inhibitor, is virtually free of the low-boiling $C_4$ hydrocarbons. The second overhead product is the wanted 1,2-butadiene in a purity of at least 97%, preferably at least 99%. The second bottom product can, in addition to the $C_5$ hydrocarbons and the total amount of the polymerization inhibitor, also comprise residual amounts of 1,2-butadiene. The polymerization inhibitor can be removed from this second bottom product by a further distillation step. The $C_5$ hydrocarbons separated off in the course of this can then be passed to material or thermal utilization. As an alternative thereto, it is also possible to feed the second bottom product directly to the thermal utilization without separating off the polymerization inhibitor.

The yield of 1,2-butadiene, based on the 1,2-butadiene present in the $C_4$ hydrocarbon fraction used, is in this embodiment at least 85%, preferably at least 87% and in particular at least 90%.

The yield can be increased still further here if the separation efficiency of the second distillation column is improved by, for example, increasing the number of theoretical plates, increasing the reflux or reducing the purity demands for the overhead product 1,2-butadiene.

The distillation columns can be equipped in both fractional distillations with plates, dumped packings or arranged packings. Both fractional distillations are usually carried out at a pressure of 0.1–1 MPa, preferably 0.2–0.8 MPa and the boiling temperatures established at this pressure.

In a second embodiment of the process according to the invention, a procedure is followed in such a manner that a) in a first fractional distillation of the polymerization-inhibitor-containing $C_4$ hydrocarbon fraction, the low-boiling $C_4$ hydrocarbons and 1,2-butadiene are taken off as first overhead product and the $C_5$ hydrocarbons and the polymerization inhibitor are taken off as first bottom product and b) the first overhead product is introduced into a second fractional distillation and there the low-boiling $C_4$ hydrocarbons are produced as second overhead product and the 1,2-butadiene is produced as second bottom product.

The first bottom product in this case, in addition to the $C_5$ hydrocarbons and the total amount of polymerization inhibitor, may also comprise residual amounts of 1,2-butadiene. The first overhead product is usually, after takeoff, firstly liquefied in a condenser and then introduced into the second fractional distillation.

It may be advantageous in this embodiment not to produce the 1,2-butadiene in the second fractional distillation via the second bottom product, but, in the second distillation column, to take it off already as a sidestream directly above the bottom, preferably some plates above the bottom. By means of this variant, it is possible to produce particularly pure 1,2-butadiene.

In this second embodiment of the process according to the invention also, the distillation columns of the two fractional distillations can have plates, dumped packings or arranged packings as internals.

The yield of 1,2-butadiene, based on the 1,2-butadiene present in the $C_4$ hydrocarbon fraction used is, in this embodiment, at least 85%, preferably at least 87%, and in particular at least 90%. The yield can here be increased still further if the separation efficiency of the second distillation column is improved by, for example, increasing the number of theoretical plates, increasing the reflux or reducing the purity demands for the overhead product 1,2-butadiene. In a third embodiment of the process according to the invention, a procedure is followed in such a manner that, in a fractional distillation of the polymerization-inhibitor-containing $C_4$ hydrocarbon fraction, all $C_4$ components boiling below 1,2-butadiene are separated off as overhead product, the $C_5$ hydrocarbons and the polymerization inhibitor are obtained as bottom product and 1,2-butadiene is taken off as sidestream. This sidestream is customarily taken off between the inlet of the $C_4$ hydrocarbon mixture to be distilled and the bottom of the distillation column.

This production of pure 1,2-butadiene from the $C_4$ hydrocarbon mixture using only one distillation column can be carried out particularly effectively if the distillation column is designed between inlet and sidestream takeoff of the 1,2-butadiene as a dividing-wall column.

The bottom product of this third embodiment of the process according to the invention, in addition to the $C_5$ hydrocarbons and the polymerization inhibitor, may also still contain residual amounts of 1,2-butadiene.

It may be advantageous in this third embodiment, to achieve a still higher purity of the 1,2-butadiene, to subject the 1,2-butadiene taken off as sidestream to a further distillation.

In the case of this third embodiment of the process according to the invention also, as internals in the distillation column, use can be made of plates, dumped packings or arranged packings.

In all three embodiments of the process according to the invention, it is advantageous that the respective fraction which, after the fractional distillation or distillations, comprises the polymerization inhibitor, is still readily pumpable and transportable and comprises no inhibitor which is crystallized out. This would be to be expected at the high inhibitor concentrations in these fractions, since the solubility limit of TBC, for example, in isopentane, which is a main component in these fractions, is only 0.5% at 20° C. and is thus markedly exceeded in the respective fractions.

EXAMPLE 1

Production of 1,2-butadiene

From 100 parts by weight of a $C_4$ hydrocarbon starting mixture which comprises TBC as polymerization inhibitor, in the first distillation column containing approximately 90 theoretical plates at a reflux of approximately 100 parts by weight, approximately 40 parts by weight of overhead product and 60 parts by weight of bottom product are obtained, the overhead product comprising less than I part by weight of 1,2-butadiene. The 60 parts by weight of the bottom product produced consist of approximately 50 parts by weight of 1,2-butadiene and approximately 10 parts by weight of $C_5$ hydrocarbons and the TBC present in the starting mixture. The bottom product is virtually free of other $C_4$ hydrocarbons (butanes, butenes, 1,3-butadiene and $C_4$ acetylenes).

The resultant first bottom product is run, without further purification, into a second distillation column having approximately 45 theoretical plates. At a reflux of approximately 250 parts by weight, the 60 parts by weight of bottom product from the first column are separated by distillation into 45 parts by weight of a second overhead product and 15 parts by weight of a second bottom product. The overhead product of the second distillation stage consists of virtually pure 1,2-butadiene (purity <99% by weight). In the bottom product of the second distillation are the $C_5$ hydrocarbons, all of the polymerization inhibitor TBC and approximately 5 parts by weight of 1,2-butadiene.

What is claimed is:

1. A process for producing relatively pure 1,2-butadiene, comprising performing at least one fractional distillation to a polymerization-inhibitor-containing hydrocarbon fraction comprising less than 100% of 1,2butadiene.

2. The process according to claim 1, wherein the polymerization inhibitor is 4-tert-butylcatechol.

3. The process according to claim 1, wherein the polymerization-inhibitor-containing hydrocarbon fraction has a boiling point in a range of from −15° C. to +40° C.

4. The process according to claim 1, wherein the polymerization-inhibitor-containing hydrocarbon fraction comprises
   0–5% by weight, of at least one saturated $C_4$ hydrocarbon,
   5–30% by weight, of at least one butene,
   10–55% by weight, of 1,3-butadiene,
   1–2% by weight, of at least one $C_4$ acetylene,
   20–65% by weight, of 1,2-butadiene,
   5–20% by weight, of at least one $C_5$ hydrocarbon, and
   0.2–2% by weight, of at least one polymerization inhibitor.

5. The process according to claim 1, wherein at least two fractional distallations to the polymerization-inhibitor-containing hydrocarbon fraction are performed, and wherein
   a) in the first fractional distillation, at least one low-boiling $C_4$ hydrocarbon is taken off as a first overhead product, and a first fraction comprising 1,2-butadiene, at least one $C_5$ hydrocarbon and the polymerization inhibitor is taken off as a first bottom product, and
   b) the first bottom product is fed to the second fractional distillation where the 1,2-butadiene is produced as a second overhead product, and the at least one $C_5$ hydrocarbon and the polymerization inhibitor are produced as a second bottom product.

6. The process according to claim 1, wherein at least two fractional distillations to the polymerization-inhibitor-containing hydrocarbon fraction are performed, and wherein
   a) in the first fractional distillation, at least one low-boiling $C_4$ hydrocarbon other than 1,2-butadiene and 1,2-butadiene are taken off as a first overhead product, and at least one $C_5$ hydrocarbon and the polymerization inhibitor are taken off as a first bottom product, and
   b) the first overhead product is introduced into the second fractional distillation where the at least one low-boiling $C_4$ hydrocarbon other than 1,2-butadiene is produced as a second overhead product, and the 1,2-butadiene is (i) taken off in a sidestream above a second bottom product or (ii) produced as the second bottom product.

7. The process according to claim 1, wherein the polymerization-inhibitor-containing hydrocarbon fraction further comprises at least one $C_4$ hydrocarbon other than 1,2butadiene and at least one $C_5$ hydrocarbon.

8. The process according to claim 7, wherein the at least one $C_4$ hydrocarbon having a boiling point which is lower than a boiling point of 1,2-butadiene is separated off as an overhead product, the at least one $C_5$ hydrocarbon and the polymerization inhibitor are produced as a bottom product, and 1,2-butadiene is taken off in a sidestream.

9. The process according to claim 8, wherein at least one fractional distillation is performed in at least one distillation column comprising an inlet portion above a bottom portion, and the sidestream is located between the inlet portion and the bottom portion.

10. The process according to claim 8, wherein the 1,2-butadiene which is taken off in the sidestream is subjected to a further distillation.

11. The process according to claim 9, wherein the at least one distillation column further comprises a dividing-wall column located between the inlet portion and the sidestream location.

12. The process according to claim 1, wherein at least two fractional distillations to the polymerization-inhibitor-containing hydrocarbon fraction are performed.

13. The process according to claim 1, wherein the relatively pure 1,2-butadiene has a purity of at least 97%.

14. A process for purifying 1,2-butadiene from a polymerization-inhibitor-containing hydrocarbon fraction comprising less than about 97% by weight of 1,2-butadiene, the process comprising the step of at least once fractionally distilling the polymerization-inhibitor-containing hydrocarbon fraction.

15. The process according to claim 14, further comprising performing a second fractional distillation to the polymerization-inhibitor-containing hydrocarbon fraction.

16. The process according to claim 14, wherein the polymerization-inhibitor-containing hydrocarbon fraction further comprises at least one $C_4$ hydrocarbon other than 1,2butadiene and at least one $C_5$ hydrocarbon.

17. The process according to claim 14, wherein the polymerization-inhibitor-containing hydrocarbon fraction comprises at least one extractive distillation residue which was drawn off from a process for producting 1,3-butadiene.

18. The process according to claim 14, wherein a yield of pure 1,2-butadiene produced, based on the weight % of 1,2-butadiene present in the polymerization-inhibitor-containing hydrocarbon fraction, is at least 85% by weight.

19. The process according to claim 14, wherein the at least once fractionally distilling is performed in at least one distillation column having a plurality of plates, a plurality of dumped packings, a plurality of arranged packings, or a mixture thereof.

20. The process according to claim 14, wherein after the 1,2-butadiene is purified, the remaining polymerization-inhibitor-containing hydrocarbon fraction is pumpable and transportable.

* * * * *

UNITED STATES PATENT AND TRADEMARK OFFICE
CERTIFICATE OF CORRECTION

PATENT NO. : 6,175,049 B1  
DATED : January 16, 2001  
INVENTOR(S) : Arnd Stüwe, Jürgen Linnemann, Jens Herwig, Christian Gabel, Bernd Hohmann, and Joachim Grub.

It is certified that error appears in the above-identified patent and that said Letters Patent is hereby corrected as shown below:

Column 2,  
Line 19, "3and" should read -- and --;

Column 5,  
Line 2, "90theoretical" should read -- 90 theoretical --;  
Line 5, "I" should read -- 1 --;  
Line 8, "10parts" should read -- 10 parts --;  
Line 15, "45theoretical" should read -- 45 theoretical --; and  
Line 21, "<99%" should -->99% --.  
Line 29, (claim 1), "1,2butadiene" should read -- 1,2-butadiene --;  
Line 48, (claim 5), "distallations" should read -- distallations --;

Column 6,  
Line 14, (claim 8),"than a boiling" should read -- than the boiling --; and  
Line 52, (claim 17), "producting" should read -- producing --.

Signed and Sealed this

Twenty-third Day of October, 2001

*Attest:*

NICHOLAS P. GODICI  
*Attesting Officer*     *Acting Director of the United States Patent and Trademark Office*